United States Patent [19]

Trivedi et al.

[11] 3,961,899
[45] June 8, 1976

[54] REACTION CONTAINER FOR CHEMICAL ANALYSIS

[75] Inventors: Ramesh C. Trivedi; Henry R. Bungay, III, both of Freehold; Paul J. Cuccolo, Toms River, all of N.J.

[73] Assignee: Worthington Biochemical Corporation, Freehold, N.J.

[22] Filed: May 16, 1975

[21] Appl. No.: 578,147

Related U.S. Application Data

[63] Continuation-in-part of Ser. No. 473,942, May 28, 1974, abandoned.

[52] U.S. Cl. ............................. 23/253 R; 23/259; 195/127
[51] Int. Cl.[2] ............................................ G01N 31/00
[58] Field of Search ........... 195/127, 139; 23/253 R, 23/253 A, 259 R

[56] References Cited
UNITED STATES PATENTS
3,691,017  9/1972  Brown et al. .................. 195/103.5 R

Primary Examiner—A. Louis Monacell
Assistant Examiner—Roeert J. Warden
Attorney, Agent, or Firm—Kenyon & Kenyon Reilly Carr & Chapin

[57] ABSTRACT

For use in measuring the extent or rate of optical density change produced by a reaction a rigid or semi-rigid disposable reaction container is disclosed of the type comprising a windowed reaction chamber adapted for the transmission of light therethrough and an auxiliary chamber that is separated from the reaction chamber except for an opening which is small enough to prevent substantial diffusion or movement of liquid from one chamber to the other when under static conditions but through which a solution of a reagent in the auxiliary chamber may be forced so as to enter the reaction chamber and commingle with a solution of another reagent and thereby trigger a reaction, improvements comprising the provision in a receptacle having side walls, end walls and a bottom wall of a projection which extends a substantial distance upwardly from the bottom wall so as to separate the lower part of the receptacle into two portions adapted to separate liquid in one of said portions from the other portion in combination with a cover having a downwardly depending divider which terminates in closely adjacent spaced relation to said projection, said projection and said divider separating said receptacle into a reaction chamber and an auxiliary chamber separated from each other except for the opening or passage that is provided by said closely spaced relation between said projection and the lower end of said divider. The parts preferably are dimensioned and arranged so that said opening is in the form of a passage of substantial length and is positioned so that nearly all of a solution in the auxiliary chamber may be forced therethrough into the reaction chamber. The receptacle preferably is in the form of one molded piece and, as sold, the cover is sealed in place with a lyophilized reagent in at least one of the chambers. Preferably the aforesaid passage is of such restricted cross-section as to prevent gravitational flow of aqueous liquid from one of said chambers to the other when the level of liquid in said chamber is substantially above the uppermost portion of said passage and is substantially above the level of any liquid in the other chamber while being large enough to permit, responsive to applied pressure, the forcing of aqueous liquid through said passage so as to be injected into the other chamber and thereby become commingled with liquid in the other chamber.

20 Claims, 11 Drawing Figures

INTRODUCING REAGENT SOLUTIONS

FIG. 10

INTRODUCING LIQUID TO DISSOLVE REAGENTS

FIG. 11

REACTION CONTAINER FOR CHEMICAL ANALYSIS

CROSS REFERENCE TO COPENDING APPLICATION

This application is a continuation-in-part of application Ser. No. 473,942, filed May 28, 1974 now abandoned.

FIELD OF THE INVENTION

This invention relates to method and means for chemical analysis and relates more especially to such method and means which lends itself to automated or semi-automated analysis procedures. The invention is especially suited for use in connection with the analysis of body fluids such as blood, urine and the like.

BACKGROUND OF THE INVENTION

Especially in the field of biochemistry, there is a very extensive demand for chemical testing from the point of view of both quantitative and qualitative analysis pertaining to substances known to have relevance to possible malfunctioning of the biochemical processes of living mammals. The number of such tests of various types which are performed each year in the U.S. is extremely great and has been estimated to be in excess of over one billion per year. Since the number of such tests heavily taxes both equipment and personnel, proposals have been made for automatic or semi-automatic testing equipment and procedures.

For use in automated procedures a disposable reaction container made of a rigid or semi-rigid material is disclosed in U.S. Pat. No. 3,691,017. It is characterized primarily by comprising a windowed reaction chamber adapted for the transmission of light therethrough and an auxiliary chamber that is separated from the reaction chamber except for an opening that is small enough to prevent the substantial diffusion or flow of liquid when in a quiescent state from one chamber to the other but through which a solution of a reagent may be caused to flow so as to commingle with solution of another reagent in the reaction chamber and thereby trigger a reaction, the disposable reaction container as a whole being of such size and slide-like configuration as to lend itself to automated equipment. The reaction container disclosed in Pat. No. 3,691,017 comprises two planar halves which, when separated from each other, are adapted to receive one or more reagent-containing solutions and on which the solution or solutions can be reduced to solid form by lyophilization. The reaction container is completed and made ready for supply to purchasers by uniting the halves as by the employment of liquid-tight, frictionally interfitting securing means.

OBJECTS OF THE INVENTION

It is an object of this invention to provide an improved disposable reaction container of the type disclosed in U.S. Pat. No. 3,691,017 which comprises an auxiliary chamber and a windowed reaction chamber separated from each other by a small opening having the functional characteristics and purposes hereinabove mentioned.

Other objects of this invention relate to improvements in a disposable reaction container of the type in question whereby improved optical accuracy may consistently be obtained and which at the same time lends itself to being readily charged with one or more reagent solutions using manual or automated equipment followed by lyophilization of the solid content of said solution.

A further object of this invention is to provide a reaction container of the type in question which lends itself to large-scale production at a substantially lesser cost as compared with that which is incident to the production of the reaction container disclosed in U.S. Pat. No. 3,691,017.

THE GENERAL NATURE OF THE INVENTION

The disposable reaction container of this invention is composed of rigid or semi-rigid material and comprises a receptacle wherein there are spaced apart side walls of substantial lateral extent, a bottom wall and end walls, the inner surfaces of which walls define a receptacle that when in upright position is open at the top and is adapted for the retention of a liquid therein. In accordance with one embodiment of this invention, there is a projection which extends a substantial distance upwardly from the bottom wall in the space between the side walls of the receptacle and which separates the lower part of the receptacle into two portions each of which is adapted for the retention of a substantial quantity of liquid therein separated from the other portion by the aforesaid projection. It is a further aspect of this invention that there is a cover for the opening at the top of the receptacle and from which a divider depends in contiguous relation to the inner surfaces of the side walls and which terminates at its lower end in closely spaced adjacent relation with respect to the aforesaid upwardly extending projection from the bottom wall so as to leave an opening or passage of restricted cross-section therebetween. The downwardly extending divider together with the upwardly extending projection serve to separate the receptacle into two chambers each of which is adapted for the retention of a liquid therein separated from the other chamber except for the aforesaid opening. One of the chambers serves as the reaction chamber and there is a transparent window in the portion of each of the side walls thereof, the windows being adapted and disposed for the successive transmission of light therethrough and through a body of liquid of predetermined thickness in said chamber that is between said windows.

The other chamber is the auxiliary chamber and preferably the lower extremity of the divider is in close proximity to the bottom wall of the auxiliary chamber so that when pressure is applied to liquid in the auxiliary chamber substantially all of the liquid may be forced through the aforesaid opening or passage and into the reaction chamber for the purpose of initiating a chemical reaction. It also is preferable that the lower end of the divider follow the contour of the projection in the bottom wall in adjacent spaced relation therewith so that the opening is caused to occur in the form of a channel or passage of substantial length, thereby minimizing the possibility of commingling solution in one of the chambers with solution in the other prior to subjecting solution in the auxiliary chamber to pressure to force it through the channel opening. Preferably also the lower end of the divider follows the contour of the projection so as to come in close proximity to the bottom wall of the container on each side of the projection.

In order to facilitate the accurate positioning of the cover with the lower end of the divider in predetermined spaced position with respect to the projection, guide means are provided for guiding the placement of the cover. Placement of the cover also preferably is assisted by causing one of the side walls of the receptacle to be somewhat higher than the other side wall by approximately the thickness of the cover. This expedient coupled with the guide means facilitates the placing of the cover in accurately located position for providing the desired dimensional characteristics of the small opening between the two chambers.

It is another aspect of the invention that the cover for the receptacle is provided with an opening which communicates with the reaction chamber and another opening which communicates with the auxiliary chamber and that these openings may be closed by a readily removable closure which preferably is in the form of a frangible sealing membrane which serves to seal the contents of the receptacle during shipment and until use but which may be readily broken away so as to permit the introduction of a solution or other liquid into the respective chambers of the reaction container. It is also a feature of the preferred practice of the invention that the container is made in one piece as by a molding operation whereby the dimensional characteristics of the container may be reproduced with a high degree of accuracy. It is also the case that the surfaces of the windows may be produced with a high degree of uniformity and of accuracy.

One of the significant improvements that is obtainable in the practice of this invention is that of improved accuracy in the production of reaction containers of the type under present consideration wherein a chemical reaction is initiated and a change in the absorption of light is noted and normally also is measured for the purpose of detecting and, if desired, measuring the amount of a reactant, as indicated by a change in the absorption of light transmitted through the reaction mixture while the reaction is taking place. For example, in analyses such as those principally contemplated herein it is common practice to employ a spectrophotometer as a source of monochromatic light in the wave length range from 290m$\mu$ to 680 m$\mu$. One wave length which is commonly used is in ultraviolet light at a wave length of essentially 340 m$\mu$. Since the concentration of the unknown reactant, such as a component in a body fluid, is determined by measuring the amount of light absorbed and since the amount of light absorbed depends and is directly proportional to the distance through which the light beam must travel, it is very important that the spacing between the inner surfaces of the windows in the reaction chamber be accurately spaced from each other by the desired predetermined distance and that this spacing be uniform not only in each unit but also as between one reaction container and another. It is also important that the inner and outer surfaces of the windows be as nearly perfectly flat as possible for even a slight amount of unevenness may result in severe distortions of the light beam. It is difficult to obtain the accuracy just described when employing the cell construction disclosed in the above-mentioned U.S. Pat. No. 3,691,017. When the construction disclosed in U.S. Pat. No. 3,691,017 is employed the two planar halves of the reaction container have to be assembled one with the other and when such assembly is attempted variations in window spacing have been experienced which, depending on their extent, result in increase in the coefficient of variations of the test for which the reaction container is used. It is also the case that when fabricating the container halves, which are employed in accordance with the construction of U.S. Pat. No. 3,691,017, difficulties have been experienced in the production of window surfaces that are sufficiently flat to prevent the occasional occurrence of light distortion. Especially when the container of the present invention is made in one piece and is produced by a molding operation, the receptacle portion of the reaction container can be reproducibly manufactured with a very high degree of accuracy both as regards the flatness of the inner surfaces in the region of the windows and the spacing between these windows. More generally, the improved construction of the reaction container of this invention makes it possible to produce reaction containers having improved optical properties as compared with that which is feasible or obtainable when employing the construction that is disclosed in U.S. Pat. No. 3,691,017.

The reaction container disclosed in U.S. Pat. No. 3,691,017 is, according to the description, intended to be used by placing a solution on one or both of the halves of the container while the halves are separated from each other and while still separated from each other the reagent contained in a quantity of deposited solution is reduced to solid form by lyophilization. However, because of the aforesaid difficulties encountered in obtaining accurate spacing between the inner surfaces of the windows in the reaction chamber the manner of use contemplated in U.S. Pat. No. 3,691,017 was modified in that the halves of the reaction container were united when empty, since the assembly could be accomplished more accurately at this time, and the reagent solutions thereafter were introduced into the reaction and auxiliary chambers, respectively, through openings in one of the margins of the container followed by lyophilization with escape of evolved vapor through said openings. This in itself was found to be inconvenient. In addition, when one solution was introduced into the auxiliary chamber and another into the reaction chamber, it was found to be necessary in order to prevent solution from flowing prematurely from one chamber into the other chamber to employ an internal configuration such that when the reaction container is tilted at an angle so that the bottom of the container is approximately 30° to the horizontal the aforesaid premature flow would not occur. Especially in large-scale production of reaction containers the necessity for filling by means of small openings in one of the margins of the container and likewise the necessity for filling while in a tilted position presented a very difficult practical problem especially as regards suitability for automated procedures. It also is the case that in order to prevent premature commingling of solutions it was necessary to maintain the containers in the tilted position during lyophilization, which position is inefficient since only one corner of the container rests on the cold plate. The reaction container of the present invention is free of such difficulties inasmuch as the reagent solutions may be initially introduced in the lower portions of the receptacle that are separated by the projection while the receptacle is resting horizontally and while the entire opening at the top is open. Moreover, lyophilization is permitted while the entire opening at the top of the receptacle is open for facilitating escape of vapors and while the entire bottom of the receptacle is resting on a cold plate. Thereafter the cover, including the divider depending therefrom, is put in place and sealed, preferably by ultrasonic sealing. On the other hand, if desired, the cover may be put in place and sealed while the receptacle is empty. In such case, by using openings that pass through the cover one may thereafter introduce a solution of a reagent into the reaction chamber or into the auxiliary chamber or both followed by lyophilization with escape of vapor through the openings. Under some circumstances this technique may be desirable, as, for example, if, during handling, there is risk of accidental spilling of solution from one portion of the receptacle into the other.

Some of the features and advantages hereinabove described may be realized when the divider instead of being integral with the cover is in contiguous integral relation with the side walls of the receptacle for in such case the relationship between the projection from the bottom wall and the lower portion of the divider can be had essentially in the same way whether the divider is integral with the cover or is already in place as an integral part of the reaction container. It has been found that even though the divider is made integral with the side walls of the reaction container so as to divide the reaction container into two chambers that are open at the top, solutions of reaction components respectively introduced into the chambers can be successfully reduced to the solid state by lyophilization. In this embodiment it is one of the features of this invention that the reaction container is divided into two chambers that are open at the top and that are separated from each other except for a passage of reduced cross section that is located in the lower portion of the reaction container but substantially above the bottom wall so that the lower part of each chamber constitutes a pocket of substantial depth below the uppermost portion of the passage between the two chambers whereby solutions containing different reaction components in substantial quantity may be introduced through the top of each chamber into each pocket without flow through the passage from one chamber to the other and thereafter separately reduced to dryness in each pocket by lyophilization. For accomplishing this feature of the invention the passage of reduced cross section may be provided in any way that is economical from the manufacturing standpoint. Thus, instead of forming the passage by cooperation between the surface of a projection from the bottom of the container and the lower extremity of a divider the passage may be defined as a preformed divider that extends from the bottom wall to the top of the reaction container.

It has been found that the passage of restricted cross section may be made with its cross sectional flow capacity of such small size that in a reaction container such as that contemplated for automated use flow therethrough of an aqueous solution can be prevented substantially completely when the tendency to flow therethrough is merely induced by gravity due to the fact that the level of liquid in one of the chambers is substantially above the uppermost portion of the passage and likewise is above the level of any liquid in the other chamber. While not dependent upon any theory advanced herein, this phenomenon is believed to be due to a surface tension effect. It has been found that the capacity to prevent gravitationally induced flow can be had even though the passage is such that, responsive to applied pressure, e.g., provided by compressed air, solution in one of the chambers may be forced through the passage so as to be injected into solution in the other chamber with sufficient force to rapidly commingle the solutions and trigger a chemical reaction between them. The prevention of premature commingling by this expedient is of advantage in carrying out the method of this invention wherein reaction components in the solid state that are respectively contained in the reaction and auxiliary chambers are dissolved by the introduction of an aqueous liquid since they can be initially dissolved without any flow of either reaction component from one chamber to the other even though the introduction of liquid into one of the compartments is continued after the level of the liquid exceeds the level of the highest portion of the passage between the two chambers. While the reaction receptacle of this invention can be constructed with the passage between the two chambers sufficiently large so that when one chamber has aqueous liquid introduced therein, it will flow through the passage into the other chamber as disclosed in U.S. Pat. No. 3,691,017 and while premature commingling can be minimized if there is no return flow, nevertheless it is preferable by the expedient aforesaid to prevent any possibility of diffusion. When flow is prevented by the smallness of the cross section of the passage it also is the case that a body of air tends to become entrapped within the passage, thereby effectively preventing any possibility of premature diffusion through the passage.

It is a further advantage incident to the employment of a passage of such small cross section as to prevent gravitational flow that, when using the embodiment of this invention wherein the divider is integral with the side walls, the solutions initially introduced into the respective chambers may be introduced until the level is substantially above the level of the uppermost portion of the passage between the two chambers, thereby permitting greater quantities of solution to be introduced into the respective chambers prior to lyophilization than otherwise would be the case. Moreover, this feature of the invention enables the reaction container to be used in the manner described even when the highest portion of the passage between the two chambers is in close proximity to the bottoms of the chambers.

Another feature of preferred practice of this invention is that of the simultaneous introduction of aqueous liquid into the reaction chamber and into the auxiliary chamber upon adding aqueous liquid to reagents respectively contained in said chambers. This feature also may be employed when solutions of reagents are initially introduced into the said chambers of the modification of the reaction container wherein the divider is an integral part thereof as initially produced. By simultaneously filling the chambers while maintaining the liquid level essentially the same flow from one chamber to the other is prevented. However, this feature of the invention preferably is employed when the cross sectional flow capacity of the passage is so small as to prevent gravitational flow from one chamber to the other since additional assurance of flow prevention is provided. It also is the case that under such circumstances prevention of flow is afforded even though the liquid levels in the two chambers may be substantially different.

The container of the present invention likewise is of advantage in that it lends itself to mass production while at the same time obtaining the aforesaid objectives of dimensional accuracy for the purposes for which the container is intended to be used. Moreover, the assembly of a receptacle containing the lyophilized reagents with the cover lends itself very well to automation by an operation wherein the cover is merely moved into place and, if desired, sealed as by ultrasonic sealing.

Further objects, features and advantages of this invention will become apparent in connection with the following description for purposes of illustration of a typical embodiment of the invention that is shown in the accompanying drawings, wherein.

Figure 1:
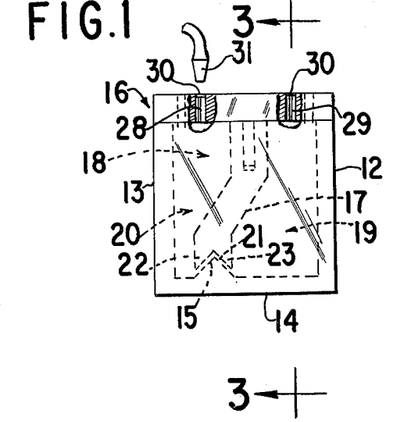
FIG. 1 is a side elevation of the assembled reaction container with broken away portions in section.
Figure 2:
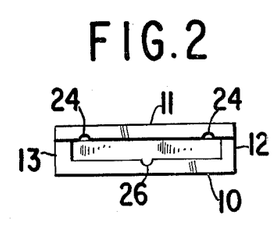
FIG. 2 shows the container of FIG. 1 with the cover removed when viewed at the top.

In the embodiment shown in FIGS. 1–7 the receptacle portion of the reaction container is in the form of a one-piece molding which comprises the side walls 10 and 11, the end walls 12 and 13 and the bottom wall 14. The projection 15 extends upwardly from the bottom wall 14 and in the embodiment shown its exterior surface is that of an inverted "V". The other essential component of the reaction container is the cover 16 from which the divider 17 depends so that when the cover is in place as shown in FIG. 1 the lower end of the divider 17 is in closely spaced proximate relation with respect to the surface of the projection 15.

The projection 15 serves to separate the lower part of the receptacle indicated generally by the reference character 18 and which is defined by the inner surfaces of the side, end and bottom walls thereof into two portions such that liquid in one of the portions is prevented from flowing into the other portion by the projection 15 when the liquid level is lower than the upward extent of the projection 15. When the cover is placed in position as shown in FIG. 1, then the divider 17 together with the projection 15 separate the receptacle 18 into two chambers, one of which is the reaction chamber 19 and the other of which is the auxiliary chamber 20. Moreover, the divider 17, either by snug contact or by heat-sealing or other sealing, serves in combination with the projection 15 to prevent liquid in either chamber 19 or chamber 20 from going into the other chamber except through the opening 21 provided between projection 15 and the terminal surface of the divider 17.

Figure 7:
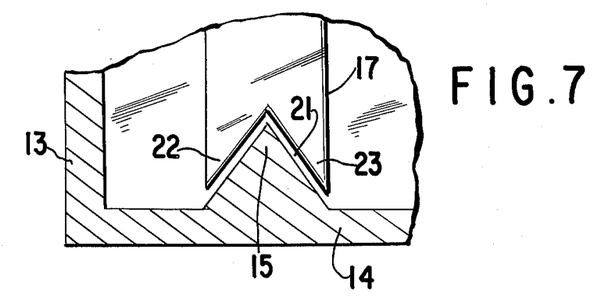
FIG. 7 is an enlarged partial sectional side elevation showing the position of the lower end of the divider in relation to the projection which extends upwardly from the bottom wall of the receptacle.

In the embodiment shown the lower end of the divider 17 is of preferred configuration wherein its contour follows the contour of the projection 15 in close proximity therewith so as to cause the opening 21 to be in the form of a channel of substantial length, thereby greatly reducing the possibility of solution moving or diffusing prematurely from one of the chambers to the other. It is also to be noted that the lower end of the divider 17 has one portion 22 which extends into close proximity to the upper surface of the bottom wall 14. This is preferable in that when pressure is applied to solution in the auxiliary chamber 20 substantially all of the solution in the auxiliary chamber may be transferred to and injected into the reaction chamber 19. It also is preferable that the portion 23 of the lower end of the divider 17 extend into close proximity to the upper surface of the bottom wall 14 since this not only serves to provide the channel opening 21 so as to have maximum length but also facilitates the movement of solution from the reaction chamber 19 into the auxiliary chamber 20 if this is desired. Sometimes it is desirable when initiating the reaction to move the solutions back and forth from one chamber to the other as by releasing and reapplying pressure or by subjecting the solution in the auxiliary chamber to a negative pressure followed by reapplied positive pressure or by alternately applying pressure to the solution in the auxiliary and reaction chambers, respectively.

It likewise is preferable that the upper and lower ends of the divider 17 be offset from each other as shown, the lower end of the divider being disposed laterally so as to be substantially closer to the end wall comprised in the auxiliary chamber than is the case with the upper end. The lower end by being closer to the end wall of the auxiliary chamber provides more efficient use of the reaction chamber since in the usual case the reaction component contained in the auxiliary chamber is a minor portion of the complete reaction mixture. However, it also is preferable that the upper portion of the auxiliary chamber have greater capacity than the lower portion in order to facilitate mixing of the reaction components contained in the respective chambers and avoid possible spill-over of reagents through the opening in the cover of the auxiliary chamber.

Figure 6:
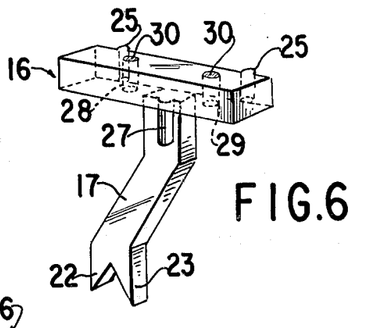
FIG. 6 is a perspective view of the cover and the divider comprised therein.

In order to facilitate the positioning of the divider 17 so that the lower end thereof is in predetermined spaced relation with respect to the projection 15, guide means preferably are employed which in the embodiment shown comprise the grooves 24 in wall 11 for accommodating the tongues 25 which protrude from the cover 16 that fit in longitudinally slideable relation therewith. There also is the groove 26 in the wall 10 which accommodates in longitudinally slideable relation therewith the tongue 27 which protrudes from the divider 17.

Figure 4:
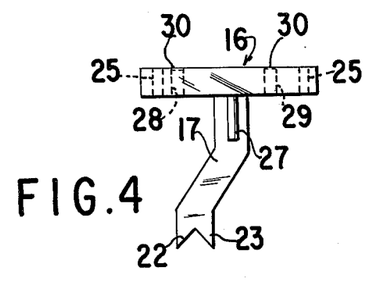
FIG. 4 is a side elevation detail view of the cover including the divider depending therefrom.
Figure 5:
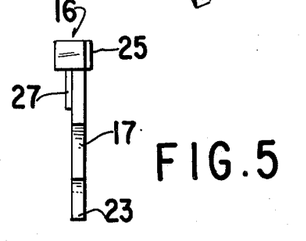
FIG. 5 is an end view of the cover shown in FIG. 4.

The cover is provided with two openings 28 and 29. The opening 28 communicates with the interior of auxiliary chamber 20 and the opening 29 communicates with the interior of the reaction chamber 19. Each of the openings is provided with a readily removable closure so that when the assembly of the reaction container has been completed with the reactants therein in lyophilized form the interior may be sealed from the atmosphere. This is preferably accomplished by providing a thin membrane 30, as best shown in FIG. 4, which extends across the opening and which may be easily ruptured when it is desired to provide access to the openings. This membrane ordinarily is automatically built into the cover when it is produced. In lieu of frangible membranes, other forms of closure for the openings in the cover may be employed such as a removable plug or stopper. Closures of this removable type are especially suitable when the reaction container is completely assembled with the contacting surfaces of the receptacle and cover permanently sealed together prior to introduction of a solution of a reaction component into the auxiliary chamber or the reaction chamber or both through openings in the cover followed by lyophilization with escape of vapors through the openings prior to the closing of the openings for storage and shipment.

The components of the reaction container are such that they may be readily mass produced with a high degree of accuracy by conventional molding operations using any rigid or semi-rigid material such as styrene or a clear acrylic resin. In the embodiment shown the inner flat surfaces of the side walls are accurate, with the result that any part of the reaction chamber which is filled with solution may be used as the windows for the transmission of light provided, of course, that the material has adequate transparency for the monochromatic light used for the contemplated test. However, if desired, the outer surfaces of the side walls in the region of the portion normally used for the transmission of light may be slightly recessed so as to minimize the possibility of becoming smudged by handling. By rigid or semi-rigid it is meant that the container structure shall have sufficient rigidity so that the distance between the window portions through which the light is transmitted is accurately maintained at a predetermined spacing. In the usual case the spacing between the windows is 5 mm and the cross section of the opening 21 may be about 9 to 17 sq. mm. The combined capacity of the reaction and auxiliary chambers when they are about 90% filled may be approximately 2.1 ml. The diameter of the openings 28 and 29 may be of the order of 0.20 inch. However, it is to be understood that the reaction container of this invention may be of any desired size and capacity depending on the test procedure for which it is to be used.

Figure 3:
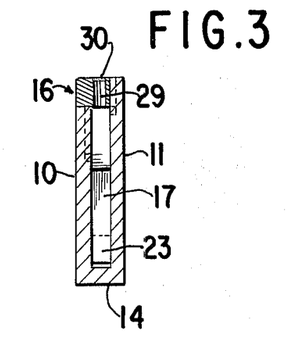
FIG. 3 is a section taken on the line 3—3 of FIG. 1.

In typical practice using the embodiment of the invention shown in FIGS. 1–7 each of the components is accurately produced to desired dimensions by a conventional molding operation and the components are assembled after a reactant in lyophilized form has been deposited in either or both of the portions of the receptacle that become the reaction and auxiliary chambers of the completed reaction container. When the reaction container is to contain a reagent in lyophilized form in each of the chambers, a measured amount of a solution of each reagent is introduced while the cover is removed, a solution of one of the reagents is placed in the lower portion of the receptacle on the side of the projection 15 that becomes comprised in the auxiliary chamber and a solution of another reaction component is placed in the lower portion of the receptacle on the other side of the projection 15 that becomes comprised in the reaction chamber, the amounts thereof being such that they are kept separated from each other by the projection 15. By way of illustration, the reagents may be those employed in an analysis for the determination of the amount of lactic dehydrogenase in a sample of blood. The reagents employed in such an analysis are lactic acid and diphosphopyridine nucleotide (DPN) and a phosphate buffer. A solution of DPN is placed in a portion of the receptacle which becomes the auxiliary chamber. The lactic acid and phosphate buffer are placed in the portion of the receptacle which becomes the reaction container. While the cover is removed the reagents are reduced to solid form by lyophilization. Thereafter, either manually or by suitable automation, the cover is put in place and in this operation the design whereby the upper margin of the side wall 11 rises higher than the upper margin of the side wall 10, as best shown in FIG. 3, facilitates the introduction of the divider 17. Upon further introduction of the divider the tongue and groove guide means hereinabove described serve to locate the cover so that the lower end of the divider becomes disposed in desired predetermined relation to the projection 15 which extends upwardly from the bottom wall. The cover may be sealed in place and the sides of the divider 17 may be established in fluid-tight relation with respect to the receptacle 18 in any desired way as by sealing. Preferably, this is accomplished by ultrasonic sealing. However, it also may be accomplished by the use of an adhesive or by the use of a solvent for the plastic material used in fabricating the container. It is one of the advantages of this invention that all parts of the reaction container may be sealed together by a single sealing operation.

When the reaction container is to be used in the performance of a test determination the membrane seals 30 are ruptured and water or an aqueous solution of another material such as a buffer is introduced through the opening 29 into the reaction container and a portion of it will flow through the channel opening 21 into the auxiliary chamber so that the liquid level in both chambers will be the same. The water or aqueous solution dissolves the lyophilized reagents. Thereafter a measured quantity of serum or other biological fluid is then introduced into the reaction chamber as by the use of a micropipet or a microsyringe and the entire reaction container is brought to the desired temperature for performing the test in question as, for example, a temperature of the order of 30°–37°C. depending on the setting that may be desired in this range. For a given test, the temperature preferably is brought within ± 0.2°C. of the reaction temperature that is desired. When the desired temperature has been attained, the opening 28 is used to introduce a puff of air under pressure into the auxiliary chamber so as to force the contents thereof into the reaction chamber and thereby trigger the reaction wherein the lactic dehydrogenase catalyzes the reaction between the lactic acid and the DPN with resultant formation of DPN in its reduced form (DPNH) which has a substantially higher density for light at 340 m$\mu$ than does DPN. The rate of any increase in optical density is measured and is a function of the amount of lactic dehydrogenase in the sample of blood serum. The rate of the reaction after it has been initiated is measured by conventional means as by moving the container into position for the passage of light at 340 m$\mu$ through the window portions of the reaction chamber and through the thickness of the reaction mass between the two windows and measuring the transmitted light at suitable stated intervals from which change in optical density may be computed. In automated procedure this may be accomplished by placing a plurality of the cells on a tray or carousel-type supporting carrier. In order to provide the puff of air, the nozzle 31 may be operatively inserted in the opening 28, the nozzle being connected to a rubber hose or a rubber bulb or the like which by compression will produce the desired puff of air. If the test procedure is automated, the nozzle can be brought into position at the desired time accompanied by the puff of air as part of the automated sequence.

Figure 8:
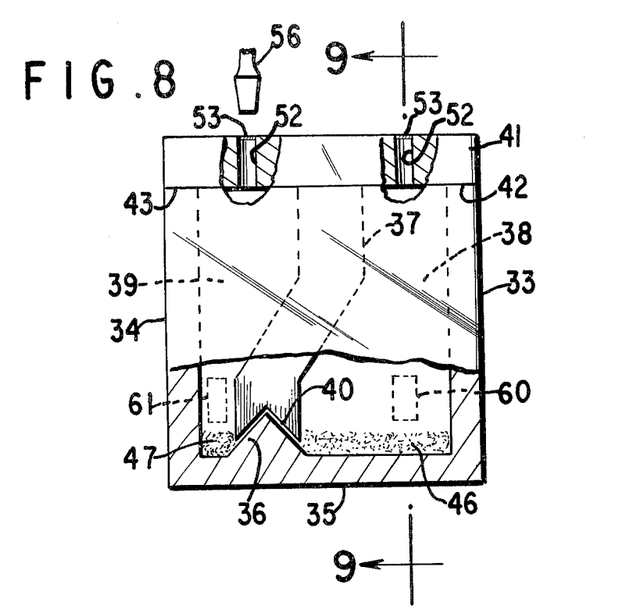
FIG. 8 is a side elevation with broken away portions in section which is similar to FIG. 1 but which shows another embodiment of the invention.
Figure 9:
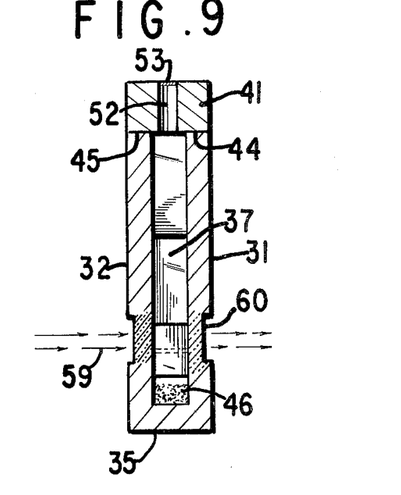
FIG. 9 is a section taken on the line 9—9 of FIG. 8.

In the modification of this invention shown in FIGS. 8-11 the reaction container comprises side walls 31 and 32 and end walls 33 and 34 and the bottom wall 35 which has the projection 36 upstanding therefrom and extending between and integral with the side walls 31 and 32. The divider 37 which divides the receptacle into a reaction chamber 38 and an auxiliary chamber 39 in this embodiment is integrally united with the extends between the side walls 31 and 32 so as to maintain liquid in the reaction and auxiliary chambers separated from each other except for the passage 40 defined by the upper surface of the projection 36 and the lowermost extremity of the divider 37 as described more fully hereinabove in connection with FIGS. 1–7. The reaction container is provided with a cover 41 which rests on the upper margins 42 and 43 of the end walls 33 and 34, respectively, and the upper margins 44 and 45 of the side walls 31 and 32, respectively. The undersurface of the cover also is flush with the upper extremity of the divider 37 so that when the cover is in place the contents of the reaction and auxiliary chambers are maintained separate from each other. The cover may be secured in place in any suitable manner as by the use of adhesive or by ultrasonic sealing. In FIG. 8 the reaction container is shown with the cover in place and with solid reaction components 46 and 47 in the bottom of the reaction chamber 38 and of the auxiliary chamber 39, respectively. Either or both may be in the form of friable solid particles. However, the reagents normally are in the form of "plugs" of solid material resulting from lyophilization of reagent solutions.

It is a feature of this invention that in the embodiment shown in FIGS. 8-11 the passage 40 is dimensioned so that its cross sectional flow capacity is sufficiently small to prevent flow of an aqueous liquid from one chamber to the other when the level of liquid in the chamber is above the uppermost portion of the passage between the chambers and likewise is above the level of any liquid in the other chamber. As mentioned hereinabove, it is believed that the resistance to flow through the passage is due to a surface tension phenomenon, although the applicants do not wish to be bound by any theory advanced herein. In has been found that such resistance to flow is not inconsistent with the cross sectional flow capacity of the passage being sufficiently large so that when solution in one chamber is subjected to applied pressure as by the use of compressed air solution in one of the chambers may be propelled through the passage so as to be injected into solution in the other chamber with sufficient force to be rapidly commingled therewith and trigger a chemical reaction. In the case of a reaction container, the dimensions of which are of the order hereinabove exemplified, the cross sectional flow capacity of the passage whereby gravitational flow is prevented while permitting forceful injection responsive to pressure is between about 1 and about 4 sq. mm, preferably between about 1 and about 2 sq. mm.

Figure 10:
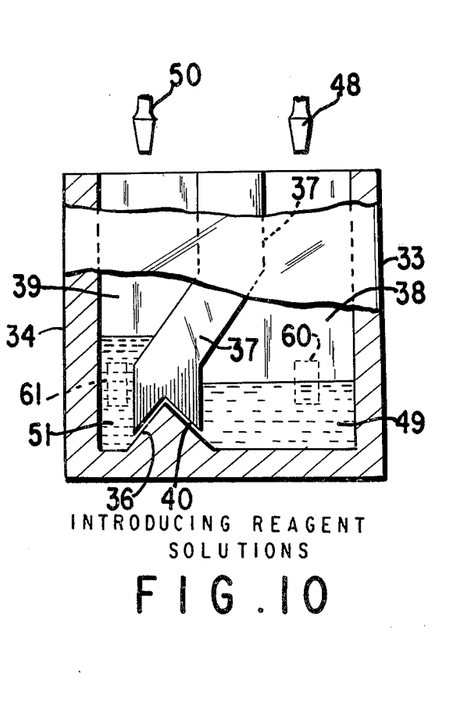
FIG. 10 is a side elevation of the embodiment shown in FIG. 8 with the cover removed and illustrating the introduction of reagent-containing solutions into the reaction and auxiliary chambers of the reaction container.

FIG. 10 illustrates the feature of this invention whereby the reagent solutions initially introduced into the respective chambers may be introduced simultaneously in a manner that expedites an automated testing procedure. For example, if the analysis is for the determination of the amount of lactic dehydrogenase in a sample of blood as described hereinabove, a solution of the lactic acid and phosphate buffer may be introduced while the cover is removed into the reaction chamber 38 by means of the filling nozzle 48 so as to accumulate the body of solution 49 in the lower portion of the reaction chamber. In like manner a solution of DPN is introducedd into the auxiliary chamber 39 by means of the filling nozzle 50 to provide an accumulated body of solution 51. Because the cross sectional flow capacity of the passage 40 is so small as to prevent gravitational flow of solution from one chamber to the other the solutions may be introduced into the reaction chamber and into the auxiliary chamber sequentially and even though the liquid level becomes substantially above the uppermost portion of the passage 40 and above the liquid level in the other chamber, as illustrated in FIG. 10, there will be no flow of solution from one chamber to the other. However, it is normally preferable in an automated procedure to accomplish the filling of the reaction chamber and the auxiliary chamber simultaneously inasmuch as in this manner less differential may be had between the liquid levels in the two chambers, thereby expediting filling and providing additional insurance against the travel of one solution from one chamber into the other. Preferably the quantities and capacities of the chambers are such that by control of timing the liquid levels in the two chambers may be maintained essentially the same at all times and by this expedient any tendency to flow from one chamber to the other is virtually eliminated even when the cross sectional flow capacity of the passage 40 is larger than that which prevents gravitational flow from one chamber to the other.

FIG. 10 illustrates an advantage of the embodiment of this invention shown in FIGS. 8–11 wherein the divider 37 is integral with the side walls 31 and 32 as compared with the embodiment of FIGS. 1–7 wherein the divider 37 is made integral with the cover and is put in place later, for when using the embodiment of FIGS. 1–7 the liquid level of the introduced solution cannot be permitted to rise above the uppermost extremity of the projection 36. However, in either embodiment of the invention a reaction container is provided wherein solutions of reagents may be introduced into pockets on either side of a divider or separator in the lower portion of the reaction container. Moreover, the introduced solutions may be reduced to the solid state by lyophilization, the solutions becoming solidified in the form of plugs as hereinabove mentioned. After the solutions have been reduced to the solid state by lyophilization when using the embodiment of FIGS. 8–11 cover 41 is put in place and united with the upper margins of the walls and divider by an adhesive, ultrasonic sealing or any other convenient sealing means. As in the embodiment of this invention shown in FIGS. 1–7, the openings 52 may be sealed over at the top with a frangible membrane 53 or with a stopper which seals the interior of each chamber during storage and shipment of the reaction container.

Figure 11:
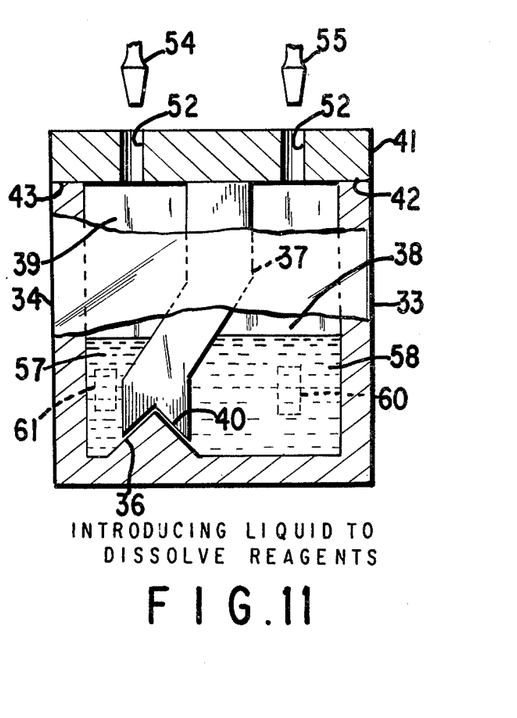
FIG. 11 is a side elevation of the embodiment shown in FIG. 8, with the cover in place and illustrating the introduction of aqueous liquids respectively into the reaction and auxiliary chambers, which liquids dissolve any solidified reagents in the respective chambers, and the introduction of liquid comprising the sample to be tested.

FIG. 11 illustrates the utility of the embodiment of this invention shown in FIGS. 8–11 at the time when it is desired to redissolve in an added aqueous liquid the reagents that are in solid state, as indicated by reference characters 46 and 47 in FIG. 8. At this time the sealing membranes 43 or other stoppers which seal the openings 52 are removed and the water or other aqueous liquid is introduced. The aqueous liquid is introduced through the openings 52 with the aid of filling nozzles 54 and 55. According to the preferred practice of this invention, the aqueous liquid is introduced into the reaction chamber 38 and into the auxiliary chamber 39 simultaneously. Preferably the rate of feed is controlled so that the liquid level in the reaction and auxiliary chambers remain essentially the same, although when the cross sectional passage 40 is such that gravitational flow therethrough is not permitted there is no necessity for doing so. When the desired amounts of liquid have been introduced a sample of blood serum or other sample to be tested is introduced into the reaction chamber, and after the reaction container and its contents have been brought to desired reaction temperature the reaction may be triggered in the manner hereinabove described in connection with FIGS. 1–7, namely, by bringing a source of compressed air via the air nozzle 56 into operative relation with the cover opening 52 which is in communication with the auxiliary chamber. Under the influence of the pressure applied by the compressed air the solution 57 contained in the auxiliary chamber is forced through the passage 40 with sufficient force to be injected into and commingled with the solution 58 in the reaction chamber, and if continued mixing is desired, the application of compressed air may be alternated with vacuum, thereby providing a pumping action whereby the commingled solutions are pumped back and forth from one chamber to the other so as to accomplish a very rapid and thorough mixing. When the reaction has been triggered as aforesaid, then the progress or extent of the reaction may be followed with the aid of a beam 59 of monochromatic light directed through the windows 60 and through the solution disposed between these windows so that any change in optical density produced by the chemical reaction between the substances in the reaction chamber may be observed and recorded.

As in the case of the embodiment shown in FIGS. 1–7, the reaction container of FIGS. 8–11 is of such configuration and nature as to lend itself to positioning in automated equipment in proper relation to the light beam. It is also the case that the reaction container also lends itself to being filled, manipulated and, if necessary, incubated using automated equipment.

When the passage 40 is of such small cross section as to prevent gravitational flow of solution therethrough, it also is of advantage that during the addition of aqueous liquid either initially or in reconstituting solid reagents a quantity of air becomes entrapped in the passage 40, thereby providing positive protection against the possibility of there being any diffusion of a substance in solution in one chamber into solution contained in the other chamber. This advantage may be realized notwithstanding that the configuration of passage 40 may be different from that shown in the drawings. However, it is preferable that the passage should be an elongated passage since an elongated passage is more effective in entrapping a body of air. If the aqueous liquids are added under sufficiently accurate control to maintain the liquid levels in the reaction and auxiliary chambers essentially the same it is possible to entrap air in an elongated passage even if it is not sufficiently small to prevent gravitational flow. However, it has been found to be preferable in the practice of this invention to employ a passage between the two chambers which is sufficiently small to prevent gravitational flow from one chamber to the other. This is the case not only in connection with the embodiment shown in FIGS. 8–11 but also in connection with the embodiment shown in FIGS. 1–7.

In the usual use of the reaction container of this invention the change in optical density is only observed in the case of solution in the reaction chamber. However, especially when the passage 40 is sufficiently small to prevent gravitational flow from one chamber to the other it is possible to provide reagents in solution in the reaction and auxiliary chambers, respectively, and trigger the reactions by the addition of a triggering chemical to each of the solutions in the respective chambers through the openings in the top. In such case the auxiliary chamber may be provided with windows 61 which are similar to the windows 60 and by passing a beam of monochromatic light not only through solution between the windows 60 but also through solution between the windows 61 the progress of the reactions in the respective chambers, as revealed by change in optical density, may be observed in this manner to carry out two determinations simultaneously in the same reaction container as, for example, if it is desired to compare the rate or extent of reaction induced by a sample to be assayed with the rate or extent of reaction in the case of a control sample. However, while the reaction container possesses this versatility it normally is employed in the manner aforesaid wherein the content of the auxiliary chamber is forced into the solution in the reaction chamber to initiate a chemical reaction.

While the reaction container of this invention is especially suitable for performing a test procedure involving an enzymatic reaction such as that between an enzyme and a substrate in the presence of such other materials as may be appropriate, e.g., a buffer or a salt, the reaction chamber of this invention is of general utility whenever the optical properties of a liquid reagent system are to be observed.

What is claimed is:

1. A disposable reaction container which is composed of rigid or semi-rigid material and which comprises:

a receptacle comprising spaced-apart side walls of substantial lateral extent, a bottom wall and end walls, the inner surfaces of said walls defining a chamber which when upright is open at the top and which is adapted for the retention of a liquid therein;

a projection which extends a substantial distance upwardly from said bottom wall and between said side walls and which separates the lower part of said chamber into two portions each of which is adapted for the retention of a substantial quantity of liquid therein separated from the other portion by said projection;

a cover for said opening at the top of said chamber;

a divider depending from said cover which is contiguous, respectively, with the inner surfaces of said side wall and which at its lower end is in closely adjacent spaced relation to said projection so as to leave an opening of restricted cross section therebetween, said divider together with said projection separating said receptacle into two chambers each of which is adapted for the retention of a liquid therein separated from the other chamber except for said opening; and a transparent window in the portion of each of said side walls comprised in one of said chambers, said windows being adapted and disposed for the successive transmission of light therethrough and through a body of liquid of predetermined thickness in said chamber.

2. The disposable reaction container according to claim 1 wherein the lower extremity of said divider is in close proximity to the bottom wall of the chamber other than said windowed chamber.

3. The disposable reaction container according to claim 1 wherein the lower end of said divider follows the contour of said projection in adjacent spaced relation thereto to provide said opening in the form of a channel of substantial length.

4. A disposable reaction container according to claim 3 wherein the lower end of said divider which follows the contour of said projection in adjacent spaced relation thereto extends into close proximity to the bottom wall of each of said chambers.

5. A disposable reaction container according to claim 1 which comprises positioning guide means effective to guide the placement of said cover so that the lower end of said divider is in fixed position in predetermined proximate spaced relation with respect to said projection.

6. A disposable reaction container according to claim 1 wherein said cover rests on the upper surface of one of the side walls and on the upper surface of each of the end walls of said receptacle, the upper surface of the other side wall of said receptacle being substantially flush with the upper surface of said cover.

7. The disposable reaction container according to claim 1 wherein said cover is fixedly secured in place across said opening at the top of said receptacle and has an opening therein providing access for the introduction of a material into one of said chambers and another opening therein providing access for the introduction of a material into the other of said chambers.

8. The disposable reaction container according to claim 7 wherein each of said openings is closed by a readily removable closure.

9. The disposable reaction container according to claim 8 wherein said closure is in the form of a readily frangible sealing membrane extending across the opening.

10. A disposable reaction container according to claim 1 wherein said side, bottom and end walls of said receptacle are in one piece.

11. A disposable reaction container according to claim 1 wherein the lower end of the divider is disposed in substantially closer proximity to the end wall of the auxiliary chamber than the upper end.

12. In a method of making a disposable reaction container comprising a reaction chamber and an auxiliary chamber separated from each other except for a small opening adapted for providing restricted flow of liquid from one chamber into the other, the improvement which comprises molding in one piece from light-transmitting material a receptacle having parallel spaced side walls of substantial lateral extent, end walls and a bottom wall, said receptacle being open at the top and having a projection extending upwardly from the bottom wall thereof which projection separates the lower part of said receptacle into two portions so that liquid cannot flow from one of said portions into the other, separately molding from one piece a cover for covering the open top of said container which cover has a divider depending therefrom that is dimensioned to be inserted between the side walls of said container flush with the inner surfaces of said receptacle and to extend into proximate closely spaced relation to said projection when said cover is covering the open top of said receptacle, placing said cover in position with attendant insertion of said divider into said receptacle with the lower end thereof positioned in proximate spaced relation with respect to said projection and so as to define a reaction chamber and an auxiliary chamber that are separated from each other except by the opening of restricted cross section where the lower end of said divider is in said proximate closely spaced relation to said projection, the portion of said reaction container occupied by said reaction chamber having windows therein that are adapted for the transmission of light therethrough and through a body of solution between them in said chamber, said windows being accurately formed during the molding of said receptacle, and by a single sealing step sealing the interfaces between the inner surfaces of said receptacle and said divider and the interfaces between said cover and the upper margins of the walls of said receptacle.

13. The method according to claim 12 wherein said sealing is accomplished by ultrasonic sealing.

14. The method according to claim 12 wherein a solution of a reagent component is placed in at least one of said portions of the receptacle and is reduced to dryness by lyophilization prior to the assembly of said cover in position covering said receptacle.

15. A disposable reaction container which is composed of rigid or semi-rigid material and which comprises:
spaced apart side walls of substantial lateral extent, a bottom wall and end walls, said side walls and said end walls being upstanding relative to said bottom wall and said side walls, said bottom wall and end walls being permanently integral with respect to each other in fluid-tight relationship,
dividing means which is contiguous with said side walls and which separates said container into two chambers each of which is adapted for the retention of liquid therein separated from the other chamber except for a passage of restricted cross section through said dividing means in the lower portion of said container,
said passage having at least a portion thereof located substantially above said bottom wall whereby each said chamber has a pocket of substantial depth at the bottom thereof adapted to retain a body of liquid therein without flow through said passage from one of said chambers to the other when said container is in upright position, and
at least one of said chambers having transparent windows therein adapted and arranged for the transmission of light therethrough and through a body of predetermined thickness of liquid within said chamber between said windows.

16. A disposable reaction container according to claim 15 wherein each of said chambers has an opening at the top that is closed by cover means and each of said pockets contains in solid form a reaction component that is different from that in the other pocket.

17. A disposable reaction container according to claim 16 wherein said reaction components, respectively, are in adherent relation to said pockets as the result of lyophilization in situ.

18. A disposable reaction container which is composed of rigid or semi-rigid material and which comprises:

spaced apart side walls of substantial lateral extent, a bottom wall and end walls, dividing means which is contiguous with said side walls and which divides said container into two chambers each of which has an opening at the top and each of which is adapted for the retention of a substantial quantity of liquid therein separated from the other except for a passage of restricted cross section in the lower portion of said container, the cross section of said passage being so restricted as to prevent gravitational flow of an aqueous liquid from one of said chambers to the other when the level of liquid in said chamber is substantially above the level of the uppermost portion of said passage and is substantially above the level of any liquid in the other chamber but is large enough to permit responsive to applied pressure the forcing of aqueous liquid from one of said chambers through said passage so as to be injected into the other chamber for becoming commingled with liquid in said other chamber, and at least one of said chambers having transparent windows therein adapted and arranged for the transmission of light therethrough and through a body of predetermined thickness of liquid in said chamber between said windows.

19. A disposable reaction container which is composed of rigid or semi-rigid material and which comprises:

a receptacle comprising spaced apart side walls of substantial lateral extent, a bottom wall and end walls, separator means which projects a substantial distance upwardly from said bottom wall and between said side walls and which separates the lower part of said receptacle into two portions each of which is adapted for the retention of a substantial quantity of liquid therein separated from the other portion by said separator means, dividing means contiguous with the inner surfaces of said side walls and which together with said separator means, said side walls and said end walls define two chambers each adapted for the retention of a substantial quantity of liquid therein separated from the other except for a passage of restricted cross section defined in part by the uppermost extremity of said separator means and adapted for the passage of liquid therethrough from one of said chambers to the other, cover means overlying said side wall, said end walls and said dividing means which is adapted and disposed to cover the upper ends, respectively, of said chambers, and a transparent window in the portion of each of said side walls comprised in one of said chambers, said windows being adapted and disposed for the successive transmission of light therethrough and through a body of liquid of predetermined thickness in said chamber.

20. A disposable reaction container according to claim 19 wherein the cross section of said passage is so reduced as to prevent gravitational flow of aqueous liquid from one of said chambers to the other when the level of said aqueous liquid in said chamber is substantially above the uppermost portion of said passage and is substantially above the level of any liquid in the other chamber but is adapted responsive to pressure applied to liquid in one of said chambers for the injection of liquid from one of said chambers through said passage into the other so as to become commingled with liquid in said other chamber.

* * * * *